United States Patent
Ikeda et al.

(10) Patent No.: US 11,199,511 B2
(45) Date of Patent: Dec. 14, 2021

(54) MEDIUM SENSOR DEVICE AND MONITORING SYSTEM

(71) Applicant: HITACHI, LTD., Tokyo (JP)

(72) Inventors: Kazuki Ikeda, Tokyo (JP); Masami Makuuchi, Tokyo (JP); Shinichi Murakami, Tokyo (JP); Ryo Kadoi, Toyko (JP); Tomoharu Nagashima, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/772,380

(22) PCT Filed: Jul. 20, 2018

(86) PCT No.: PCT/JP2018/027246
§ 371 (c)(1),
(2) Date: Jun. 12, 2020

(87) PCT Pub. No.: WO2019/130632
PCT Pub. Date: Jul. 4, 2019

(65) Prior Publication Data
US 2021/0109037 A1   Apr. 15, 2021

(30) Foreign Application Priority Data
Dec. 26, 2017 (JP) .............................. JP2017-248590

(51) Int. Cl.
*G01R 27/04* (2006.01)
*G01R 27/32* (2006.01)
(Continued)

(52) U.S. Cl.
CPC ......... *G01N 22/00* (2013.01); *G01N 21/3563* (2013.01); *G01N 21/3581* (2013.01);
(Continued)

(58) Field of Classification Search
CPC .... G01N 22/00; G01N 22/04; G01N 21/3581; G01N 22/02; G01N 21/3563;
(Continued)

(56) References Cited

U.S. PATENT DOCUMENTS 10,073,074 B1 *  9/2018  Kumar .................. G01N 27/026
2015/0181315 A1 *  6/2015  Vuran ................... G01S 13/885
                                                                    340/870.3
(Continued)

FOREIGN PATENT DOCUMENTS

| CN | 101339151 A | 1/2009 |
|---|---|---|
| EP | 3196676 A1 | 7/2017 |
| JP | 2017-110983 A | 6/2017 |

OTHER PUBLICATIONS

Chinese Office Action dated Aug. 5, 2021 for Chinese Patent Application No. 201880079233.1.
(Continued)

*Primary Examiner* — Raul J Rios Russo
(74) *Attorney, Agent, or Firm* — Volpe Koenig

(57) ABSTRACT

Provided is a technique for specifying a medium more simply. A medium sensor device includes an antenna, a storage unit that stores a medium identification table in which a medium corresponding to an antenna impedance has been determined beforehand, and a medium specification unit that specifies the impedance of the antenna and specifies a medium in the vicinity of the antenna by referring to the medium identification table.

12 Claims, 19 Drawing Sheets

(51) Int. Cl.
*G01N 22/00* (2006.01)
*G01N 33/24* (2006.01)
*H01Q 1/04* (2006.01)
*H01Q 1/32* (2006.01)
*G01N 21/3581* (2014.01)
*G01N 22/02* (2006.01)
*G01N 21/3563* (2014.01)
*G01N 27/02* (2006.01)
*G01N 22/04* (2006.01)
*A61B 5/05* (2021.01)
*A61B 5/0507* (2021.01)

(52) U.S. Cl.
CPC .............. *G01N 22/02* (2013.01); *G01N 27/02* (2013.01); *G01N 33/24* (2013.01); *H01Q 1/04* (2013.01); *H01Q 1/3233* (2013.01); *A61B 5/05* (2013.01); *A61B 5/0507* (2013.01); *G01N 22/04* (2013.01)

(58) Field of Classification Search
CPC .......... G01N 27/02; G01N 33/24; A61B 5/05; A61B 5/0507; H01Q 1/04; H01Q 1/3233; G01R 27/02; G01V 3/12; G01W 1/00
USPC ... 324/76.11–76.83, 459, 600, 629, 637, 639
See application file for complete search history.

(56) References Cited

U.S. PATENT DOCUMENTS

2016/0077029 A1 3/2016 Dempster et al.
2017/0176587 A1 6/2017 Aoki et al.
2018/0224382 A1* 8/2018 Golombek ............ G01N 22/04

OTHER PUBLICATIONS

Partial Supplementary European Search Report dated Oct. 15, 2021 for European Patent Application No. 18895270.9.

* cited by examiner

FIG. 4

MEDIUM IDENTIFICATION TABLE 61

| RANGE OF IMPEDANCE (Ω) | MEDIUM (TARGET) |
|---|---|
| LESS THAN 16.5 | WATER |
| 16.5 OR MORE AND LESS THAN 32.5 | WET SNOW (HAVING WATER CONTENT OF ABOUT 25%) |
| 32.5 OR MORE AND LESS THAN 52.0 | SNOW SLUSH (HAVING WATER CONTENT OF ABOUT 10%) |
| 52.0 OR MORE AND LESS THAN 65.5 | DRY SNOW |
| 65.5 OR MORE | AIR |

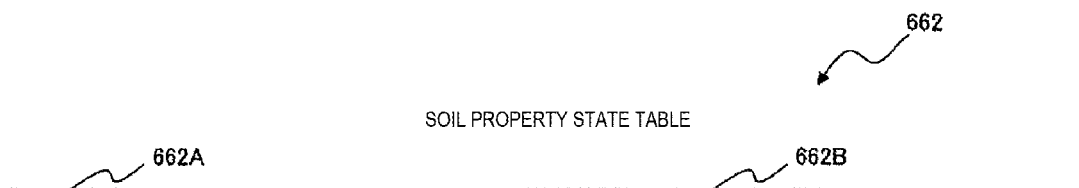

SOIL PROPERTY STATE TABLE

| TIME | SENSOR NUMBER | | | | | |
|---|---|---|---|---|---|---|
| | #001 | #002 | #003 | #004 | #005 | ... |
| 2017/12/22 12:00 | HAVING WATER CONTENT OF 0% | HAVING WATER CONTENT OF 0% | AIR | WATER | HAVING WATER CONTENT OF 0% | ... |
| 2017/12/23 12:00: | HAVING WATER CONTENT OF 0% | HAVING WATER CONTENT OF 0% | AIR | WATER | HAVING WATER CONTENT OF 10% | ... |
| 2017/12/24 12:00 | HAVING WATER CONTENT OF 0% | AIR | AIR | WATER | HAVING WATER CONTENT OF 10% | ... |
| 2017/12/25 12:00 | HAVING WATER CONTENT OF 0% | AIR | WATER | WATER | HAVING WATER CONTENT OF 20% | ... |
| 2017/12/26 12:00 | HAVING WATER CONTENT OF 0% | AIR | WATER | WATER | WATER | ... |
| ... | ... | ... | ... | ... | ... | ... |

MEDIUM SENSOR DEVICE AND MONITORING SYSTEM

TECHNICAL FIELD

The present invention relates to a technique of a medium sensor device and a monitoring system. The present invention claims priority of Japanese Patent Application number 2017-248590, filed on Dec. 26, 2017, the entire subject content of which is incorporated herein by reference in countries where incorporation by reference to patent literatures is permitted.

BACKGROUND ART

PTL 1 discloses a snow quality measuring apparatus including a plurality of reflectors that are respectively arranged at a plurality of predetermined heights above the ground, at least one transmitter that emits radio waves towards the plurality of reflectors, at least one receiver that receives reflected waves of the radio waves from the plurality of reflectors, and a measuring device that measures quality of snow accumulated on the ground at the plurality of predetermined heights based on the reflected waves received by the receiver from the plurality of reflectors.

CITATION LIST

Patent Literature

PTL 1: JP-A-2017-110983

SUMMARY OF INVENTION

Technical Problem

In the technique disclosed in PTL 1, since a height of snow accumulated on the ground is measured by receiving reflected waves from the reflectors at a plurality of heights above the ground, the reflectors need to be provided at measurement positions beforehand, and an effect cannot be obtained in a case in which there are a large number of measurement positions, in a case of positions where it is difficult to provide the reflectors, or the like.

An object of the invention is to provide a technique for specifying a medium more simply.

Solution to Problem

The present application includes a plurality of methods for solving at least a part of the problems described above, and an example is as follows. In order to solve the above problems, a medium sensor device according to an aspect of the invention includes an antenna, a storage unit that stores a medium identification table in which a medium corresponding to an impedance of the antenna has been determined beforehand, and a medium specification unit that specifies an impedance of the antenna and specifies a medium in the vicinity of the antenna by referring to the medium identification table.

Advantageous Effect

According to the invention, the medium can be specified more simply. Problems, configurations, and effects other than those described above will become apparent from the following description of embodiments.

BRIEF DESCRIPTION OF DRAWINGS

FIG. 4 is a diagram showing an example of a data structure of a medium identification table.

FIG. 15 is a diagram showing an example of a data structure of a soil property state table.

DESCRIPTION OF EMBODIMENTS

Figure 1:
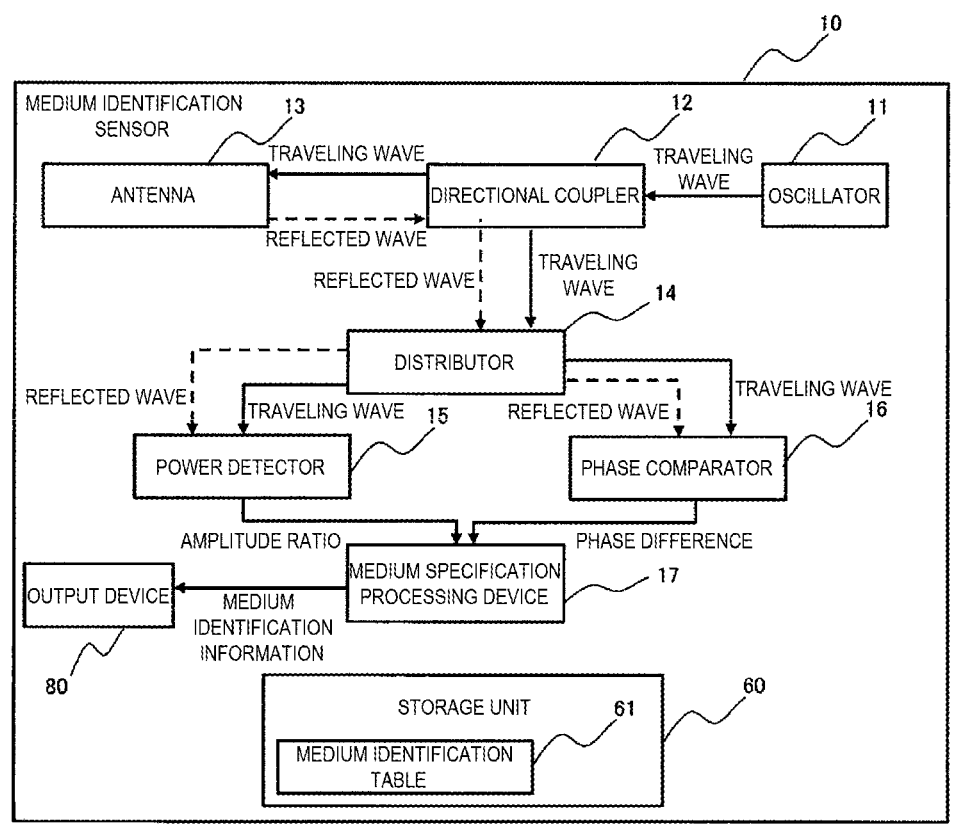
FIG. 1 is a diagram showing a configuration example of a medium identification sensor.

Hereinafter, an embodiment of the invention will be described with reference to the drawings. In all the drawings for describing the embodiment, the same components are denoted by the same reference numerals in principle, and repetitive descriptions thereof may be omitted. In the following embodiment, it is needless to say that constituent elements (including element steps and the like) are not necessarily essential unless otherwise particularly specified and considered as essential in principle. It is needless to say that expressions "formed of A", "made of A", "having A", and "including A" do not exclude elements other than A unless otherwise specified that A is the only element. Similarly, in the following embodiment, shapes, position relationships, and the like of constituent elements and the like include those substantially approximate or similar to the shapes or the like unless otherwise particularly specified and considered in principle.

FIG. 1 is a diagram showing a configuration example of a medium identification sensor. A medium identification sensor 10 includes an oscillator 11 that generates traveling waves, a directional coupler 12 that inputs and outputs traveling waves and reflected waves, an antenna 13 that radiates an electromagnetic field supplied by traveling waves to the vicinity and generates reflected waves, a distributor 14 that receives the reflected waves and the traveling waves from the directional coupler 12 and distributes the reflected waves and the traveling waves to another device, a power detector 15 that receives the reflected waves and the traveling waves from the distributor 14, detects power of the reflected waves and the traveling waves, and outputs an amplitude ratio, a phase comparator 16 that receives the reflected waves and the traveling waves from the distributor 14 and outputs a phase difference between the reflected waves and the traveling waves, a medium specification processing device 17 that acquires the amplitude ratio from the power detector 15 and the phase difference from the phase comparator 16 to specify a medium in the vicinity of the antenna 13, an output device 80 that receives and outputs medium identification information used for identifying the specified medium, and a storage unit 60 that stores a medium identification table 61 in which a medium estimated according to an impedance range has been associated with the impedance range beforehand.

The medium identification sensor 10 can radiate a weak electromagnetic field (traveling waves) from the antenna 13. On the other hand, an impedance of the antenna 13 changes according to a difference in surrounding mediums. The medium specification processing device 17 specifies an impedance based on reflected waves and traveling waves. The medium specification processing device 17 estimates a medium in the vicinity of the antenna 13 for the specified impedance by referring to the medium identification table 61 in which a medium estimated according to an impedance range has been associated with the impedance range beforehand.

Figure 2:
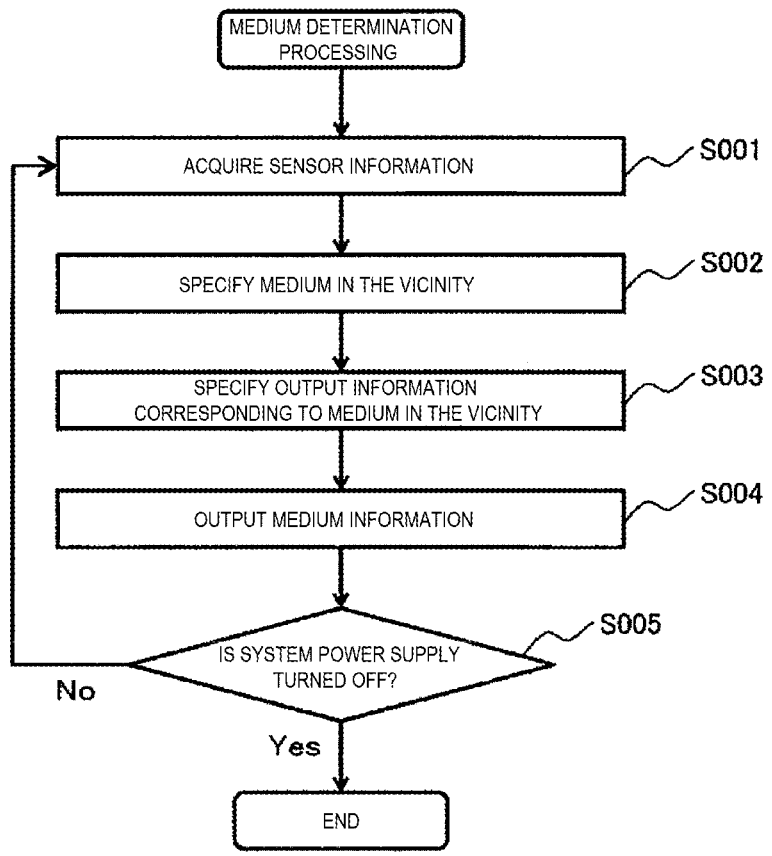
FIG. 2 is a flowchart showing an example of medium determination processing.

FIG. 2 is a flowchart showing an example of medium determination processing. The medium determination processing is started at a predetermined frequency such as once every 10 seconds.

First, the medium specification processing device 17 acquires sensor information (step S001). Specifically, the medium specification processing device 17 acquires an amplitude ratio of reflected waves to traveling waves from the power detector 15 and a phase difference between the traveling waves and the reflected waves from the phase comparator 16.

Then, the medium specification processing device 17 specifies a medium in the vicinity (step S002). Specifically, the medium specification processing device 17 calculates an impedance of the antenna 13 using the amplitude ratio and the phase difference acquired in step S001. Next, the medium specification processing device 17 specifies a range to which the calculated impedance belongs by referring to the medium identification table 61 which will be described later, and specifies a predetermined medium in the range as a medium in the vicinity of the antenna 13.

Then, the medium specification processing device 17 specifies output information corresponding to the medium in the vicinity (step S003). Specifically, the medium specification processing device 17 specifies, for the medium in the vicinity specified in step S002, predetermined information such as a display (for example, a screen display of slippery floor or a screen display of water leakage), an audio output (for example, an audio guidance "icy surface, please watch your step"), or an alert notification to a monitoring system.

Then, the output device 80 outputs medium information (step S004). Specifically, the output device 80 outputs the predetermined information such as the display or the audio output specified in step S003.

Next, the medium specification processing device 17 determines whether a system power supply is turned off (step S005). When the system power supply is turned off ("Yes" in step S005), the medium specification processing device 17 ends the medium determination processing. When the system power supply is not turned off ("No" in step S005), the medium specification processing device 17 returns a control to step S001.

A flow of the medium determination processing is described above. According to the medium determination processing, a medium can be specified based on an impedance changed by the medium in the vicinity of the antenna 13. Since the medium identification sensor that performs the medium determination processing does not require other equipment such as a reflection plate in snow and can specify a medium in a non-contact manner, the medium can be specified more simply. Since it has been found that a medium water content greatly affects an impedance mainly, the medium water content may be applied to a road surface condition which will be described later, a soil property change on a back surface of a tunnel lining, and the like.

Figure 3:
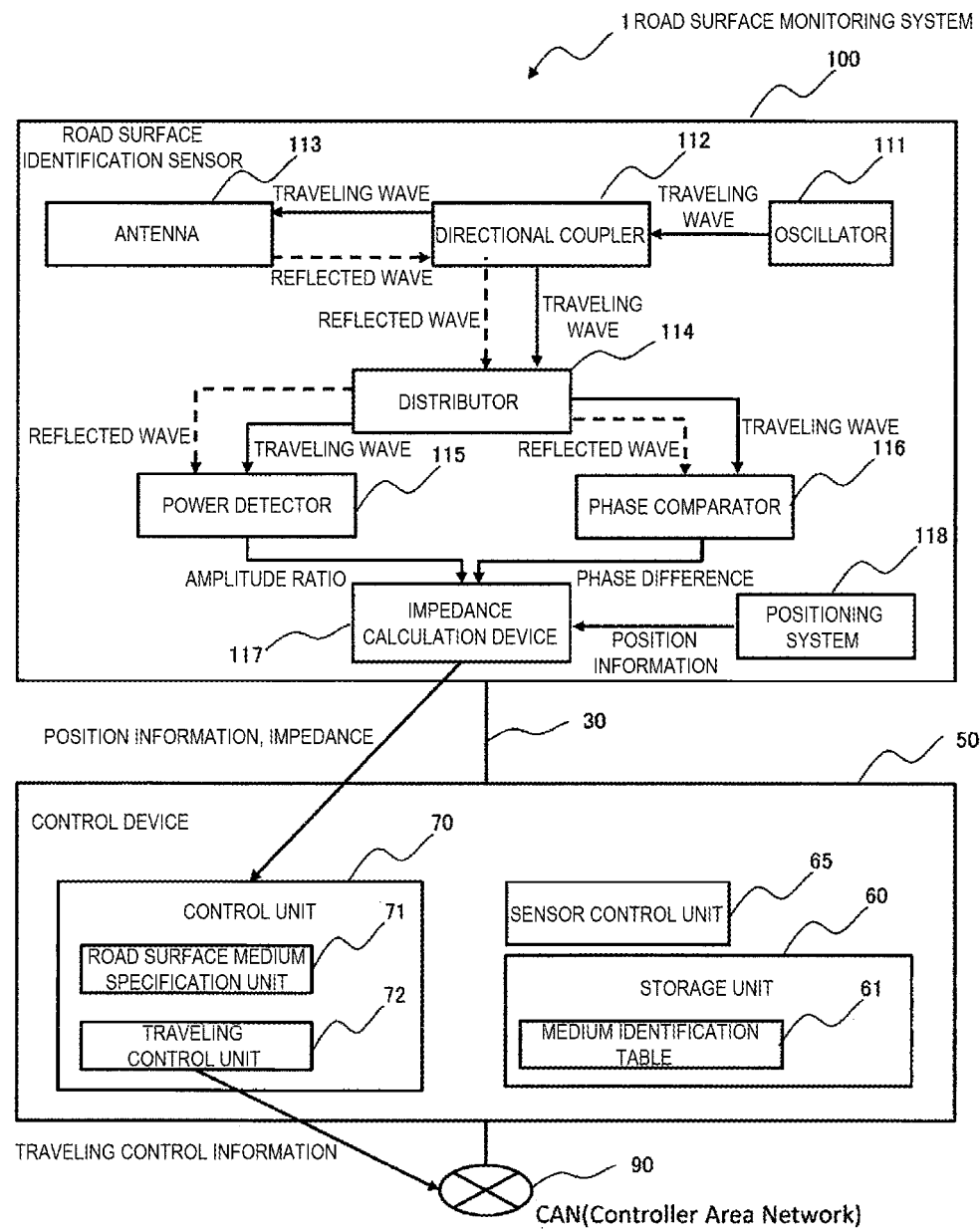
FIG. 3 is a diagram showing a configuration example of a road surface monitoring system.

FIG. 3 is a diagram showing a configuration example of a road surface monitoring system. In a road surface monitoring system 1, the medium identification sensor described above is applied and mounted to a vehicle and identifies a road surface medium (such as snow, water, and air (without snow)), and a traveling control (for example, change a minimum distance between vehicles, change a brake assist strength, or change a cruising speed) corresponding to the road surface medium is performed.

The road surface monitoring system 1 includes one or a plurality of road surface identification sensors 100, and a control device 50 connected to the road surface identification sensor 100 by a cable 30 such as a coaxial cable. The control device 50 is connected to a control network 90 such as a controller area network (CAN).

The road surface identification sensor 100 includes an oscillator 111 that generates traveling waves, a directional coupler 112 that inputs and outputs traveling waves and reflected waves, an antenna 113 that radiates an electromagnetic field supplied by traveling waves to the vicinity and generates reflected waves, a distributor 114 that receives the reflected waves and the traveling waves from the directional coupler 112 and distributes the reflected waves and the traveling waves to another device, a power detector 115 that receives the reflected waves and the traveling waves from the distributor 114, detects power of the reflected waves and the traveling waves, and outputs an amplitude ratio, a phase comparator 116 that receives the reflected waves and the traveling waves from the distributor 114 and outputs a phase difference between the reflected waves and the traveling waves, an impedance calculation device 117 that acquires the amplitude ratio from the power detector 115 and the phase difference from the phase comparator 116 and calculates an impedance of the antenna 113, and a positioning system 118 that acquires position information using satellite waves such as a global positioning system (GPS).

The control device 50 includes a sensor control unit 65 that controls the road surface identification sensor 100, a control unit 70 that specifies a road surface medium and controls traveling of a vehicle on which the road surface identification sensor 100 is mounted, and the storage unit 60 that stores the medium identification table 61 in which a medium estimated according to an impedance range has been associated with the impedance range beforehand.

The road surface identification sensor 100 can radiate an electromagnetic field (traveling waves) from the antenna 113. On the other hand, an impedance of the antenna 113 changes according to a difference in surrounding mediums. The impedance calculation device 117 specifies an impedance based on reflected waves and traveling waves, and transfers the impedance and the position information measured by the positioning system 118 to the control device 50 via the cable 30.

FIG. 4 is a diagram showing an example of a data structure of the medium identification table. In the medium identification table 61, an impedance range 61A that is information for specifying an impedance range and a medium 61B serving as a target medium are stored in association with each other. The medium identification table 61 stores information indicating, for example, "water" is present in the vicinity of the antenna 113 when an impedance is less than 16.5 ohms (Ω), a so-called "wet snow" having a water content of about 25% is present in the vicinity of the antenna 113 when an impedance is 16.5Ω or more and less than 32.5Ω. The information shown in FIG. 4 is just an example, and if there is a significant boundary value that can distinguish other mediums, an impedance range may be specified according to the value.

The control unit 70 of the control device 50 includes a road surface medium specification unit 71 and a traveling control unit 72. The road surface medium specification unit 71 estimates a road surface medium in a specified impedance range by referring to the medium identification table 61 in which a medium estimated according to an impedance range has been associated with the impedance range beforehand. The traveling control unit 72 issues an instruction to an engine control unit (ECU) (not shown) or the like via the control network 90 so as to perform a traveling control (for example, change a minimum distance between vehicles, change a brake assist strength, or change a cruising speed) corresponding to a road surface medium (such as snow, water, and air (without snow)).

Figure 5:
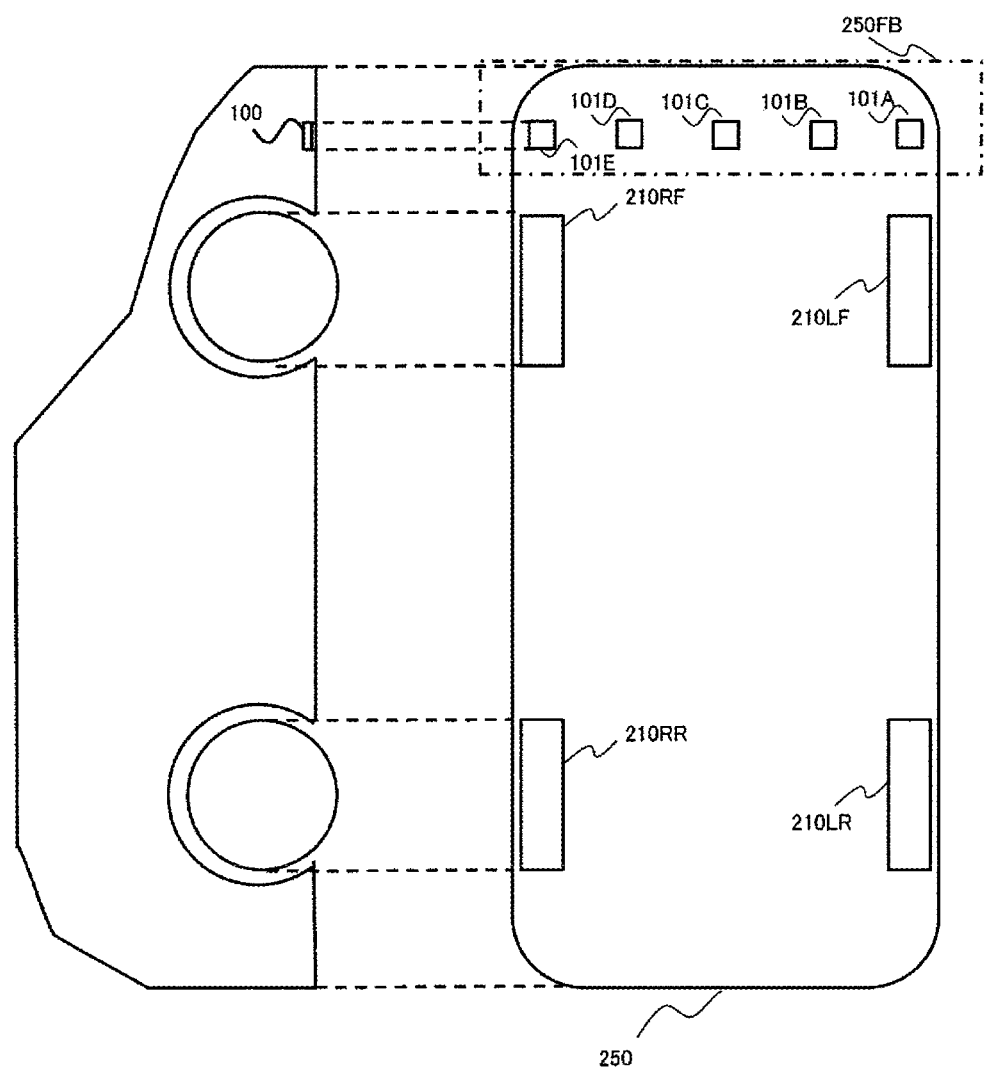
FIG. 5 is a diagram showing a sensor to vehicle mounting example.

FIG. 5 is a diagram showing a sensor to vehicle mounting example. In a sensor to vehicle mounting example 200, the road surface identification sensor 100 is mounted in the vicinity of a bottom surface of a front bumper 250FB of a vehicle 250. When a plurality of (preferably 5) road surface identification sensors 100 are mounted, it is desirable that the road surface identification sensors 100 are mounted at least at a sensor position 101E right ahead of a right front tire 210RF and at a sensor position 101A right ahead of a left front tire 210LF. This is because a road surface medium that is actually in contact with a tire can be known particularly when there is a rut.

Mounting positions of the road surface identification sensors 100 are not limited to the positions described above. For example, when only one road surface identification sensor 100 is mounted in the vehicle 250, the road surface identification sensor 100 may be mounted at a sensor position 101C in the vicinity of the center of the bottom surface of the front bumper 250FB, or may be mounted at another position due to a layout restriction.

Figure 6:
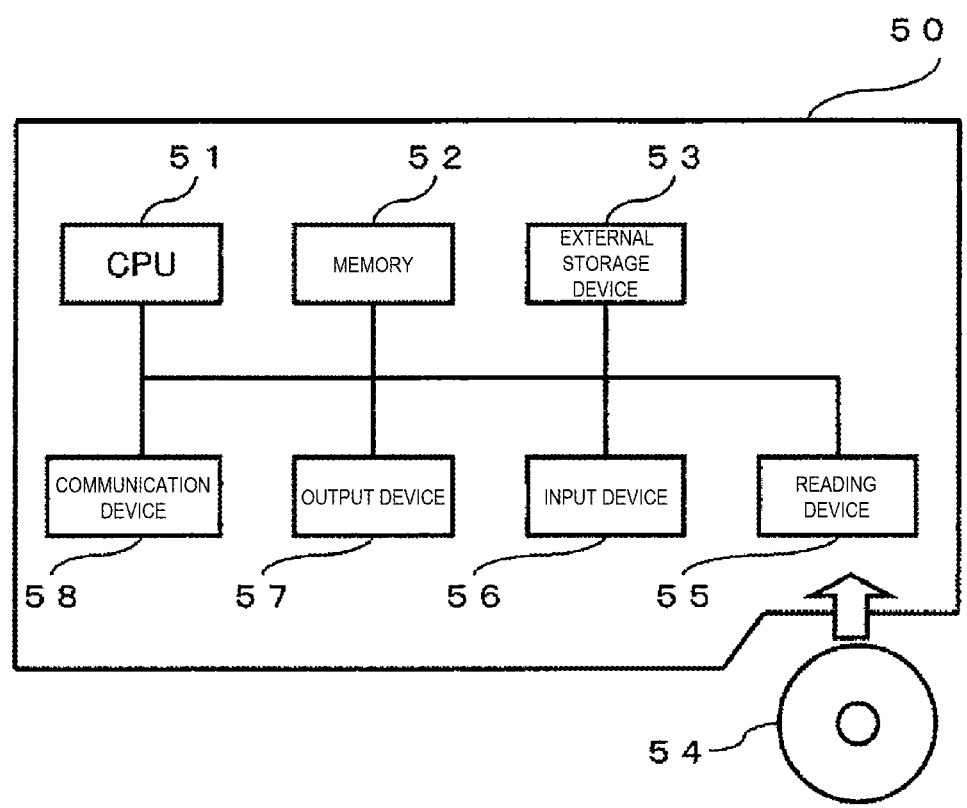
FIG. 6 is a diagram showing an example of a hardware structure of a control device.

FIG. 6 is a diagram showing an example of a hardware structure of the control device. The control device 50 can be implemented by a computer including a central processing unit (CPU) 51, a memory 52, an external storage device 53 such as a hard disk drive (HDD), a reading device 55 that reads information from and writes information into a portable storage medium 54 such as a compact disk (CD) and a digital versatile disk (DVD), an input device 56 such as a keyboard, a mouse, and a barcode reader, an output device 57 such as a display, and a communication device 58 that communicates with another computer via a communication network such as the control network 90, or the control device 50 can be implemented by a computer system including a plurality of such computers.

For example, the control unit 70 and the sensor control unit 65 may be implemented by loading a predetermined program stored in the external storage device 53 into the memory 52 and executing the program by the CPU 51. The storage unit 60 may be implemented by using the memory 52 or the external storage device 53 by the CPU 51.

The predetermined program may be downloaded from the storage medium 54 to the external storage device 53 via the reading device 55, and then may be loaded into the memory 52 and executed by the CPU 51.

Alternatively, the predetermined program may be directly loaded from the storage medium 54 into the memory 52 via the reading device 55 and executed by the CPU 51.

The control device 50 is not limited thereto, and may be implemented by an application specific integrated circuit (ASIC), a microcomputer, or the like.

Figure 7:
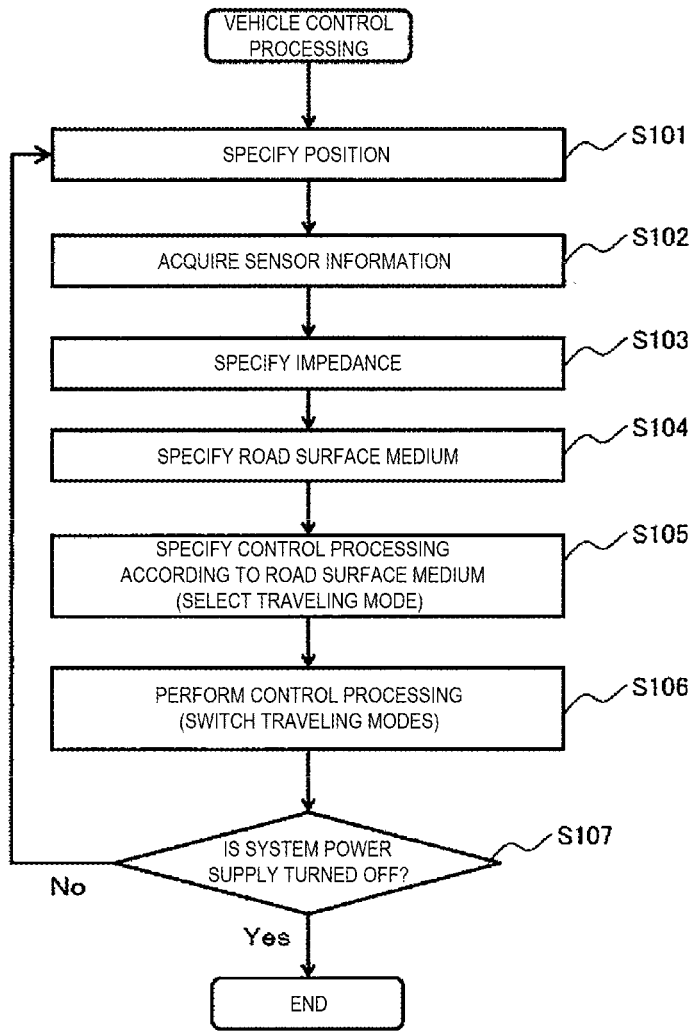
FIG. 7 is a flowchart showing an example of vehicle control processing.

FIG. 7 is a flowchart showing an example of vehicle control processing. The vehicle control processing is started at a predetermined frequency such as once every 10 seconds.

First, the positioning system 118 specifies a position (step S101). Specifically, the positioning system 118 receives information from a satellite such as a GPS and specifies a current location. Then, the impedance calculation device 117 acquires sensor information (step S102). Specifically, the impedance calculation device 117 acquires an amplitude ratio of reflected waves to traveling waves from the power detector 115 and a phase difference between the traveling waves and the reflected waves from the phase comparator 116.

Next, the impedance calculation device 117 specifies an impedance (step S103). Specifically, the impedance calculation device 117 calculates an impedance of the antenna 113 using the amplitude ratio and the phase difference acquired in step S102, and transmits the calculated impedance and position information to the control device 50 via the cable 30.

Then, the road surface medium specification unit 71 specifies a road surface medium (step S104). Specifically, the road surface medium specification unit 71 specifies a range to which the calculated impedance belongs by referring to the medium identification table 61, and specifies a predetermined medium in the range as a road surface medium in the vicinity of the antenna 113.

Next, the road surface medium specification unit 71 specifies control processing corresponding to a road surface medium (step S105). Specifically, the road surface medium specification unit 71 specifies a predetermined traveling mode of a traveling control corresponding to the road surface medium specified in step S104. In the traveling mode, auxiliary modes of a traveling support (a traveling restriction) corresponding to various road surface conditions such as "snow road surface traveling", "wet road surface traveling", "icy road surface traveling", and "expressway traveling" are provided beforehand. The traveling mode is used in a traveling control of the vehicle 250.

Then, the traveling control unit 72 performs the control processing (step S106). Specifically, the traveling control unit 72 outputs an instruction of a predetermined traveling control corresponding to the traveling control mode specified in step S105 to an ECU or the like.

Next, the road surface medium specification unit 71 determines whether the system power supply is turned off (step S107). When the system power supply is turned off ("Yes" in step S107), the road surface medium specification unit 71 ends the vehicle control processing. When the system power supply is not turned off ("No" in step S107), the road surface medium specification unit 71 returns the control to step S101.

A flow of the vehicle control processing is described above. According to the vehicle control processing, the road surface medium can be specified based on the impedance changed by the road surface medium in the vicinity of the antenna 113. Since the road surface identification sensor 100 used in the traveling control processing does not require other equipment such as a reflection plate in snow and can specify a medium in a non-contact manner, the road surface identification sensor 100 can be used for a general road surface and a medium can be specified more simply.

Figure 8:
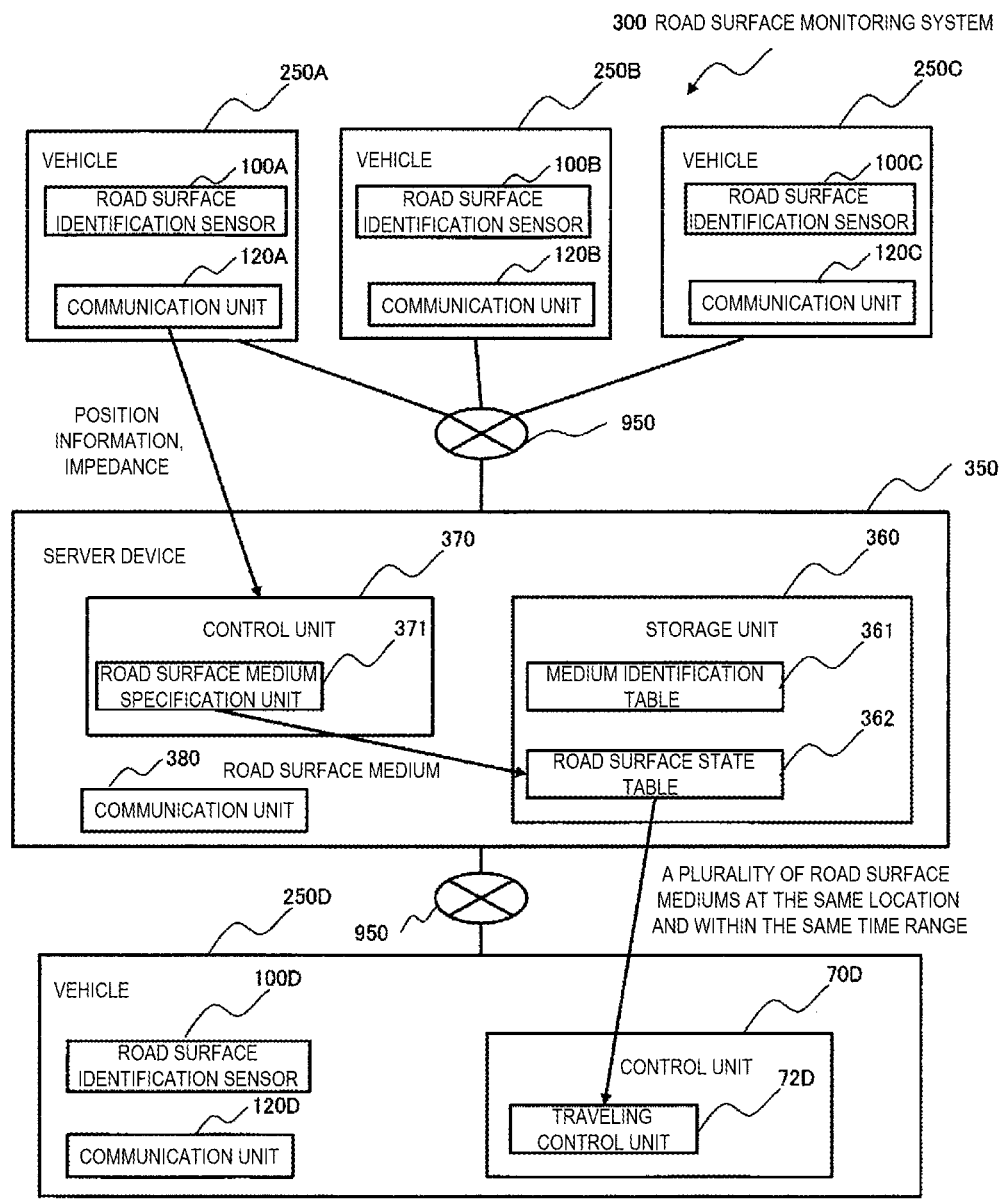
FIG. 8 is a diagram showing another example of a road surface monitoring system.

FIG. 8 is a diagram showing another example of a road surface monitoring system. In a road surface monitoring system 300, a road surface medium is shared among a plurality of vehicles to each of which the medium identification sensor described above is applied, and a traveling control (for example, change a minimum distance between the vehicles, change a brake assist strength, change a cruising speed, or change a traveling route to avoid danger when danger occurs in a traveling area to be arrived along an assumed traveling route) corresponding to the road surface medium is performed.

In the road surface monitoring system 300, a plurality of vehicles 250 (hereinafter, respectively described as a vehicle 250A, a vehicle 250B, a vehicle 250C, and a vehicle 250D when the plurality of vehicles 250 need to be described individually) and a server device 350 are communicably connected via a network 950. The road surface identification sensors 100 (hereinafter, respectively described as a road surface identification sensor 100A, a road surface identification sensor 100B, a road surface identification sensor 100C, and a road surface identification sensor 100D when the road surface identification sensors 100 need to be described individually) and communication units 120 (hereinafter, respectively described as a communication unit 120A, a communication unit 120B, a communication unit 120C, and a communication unit 120D when the communication units 120 need to be described individually) are respectively mounted in the vehicle 250A, the vehicle 250B, the vehicle 250C, and the vehicle 250D. In addition to the road surface identification sensor 100D and the communication unit 120D, a control unit 70D including a traveling control unit 72D is mounted in the vehicle 250D.

The network 950 is a public network including a so-called Internet or a mobile phone network. Similarly with the road surface identification sensor 100 described above, the road surface identification sensor 100 outputs position information and impedance information to the communication unit 120. The communication unit 120 transmits the position information and the impedance information to the server device 350 via the network 950.

The traveling control unit 72D provided in the control unit 70D acquires a plurality of road surface mediums at the same location and within the same time range by referring to a road surface state table 362 held by the server device 350, and uses the road surface mediums in a traveling control. Specifically, the traveling control unit 72D issues an instruction to an engine control unit (ECU) (not shown) or the like via a control network (not shown) so as to perform a traveling control (for example, change a minimum distance between vehicles, change a brake assist strength, or change a cruising speed) corresponding to a road surface medium (such as snow, water, and air (without snow)).

For example, when a plurality of vehicles have passed through a predetermined location within a predetermined time range and information indicating a road surface medium at the location is "wet snow" or "water" is transmitted from the plurality of vehicles, the traveling control unit 72D estimates that the road surface medium is "wet snow" based on a fail-safe viewpoint and switches a traveling control of the vehicles to a traveling mode corresponding to "wet snow" before the vehicles arrive at the location. Without depending on the fail-safe viewpoint, the road surface medium may be specified by weighting or the like, or may be simply specified by a majority decision.

The server device 350 includes at least a storage unit 360, a control unit 370, and a communication unit 380. The storage unit 360 stores a medium identification table 361 and a road surface state table 362. The medium identification table 361 has a similar data structure as the medium identification table 61 described above.

Figure 9:
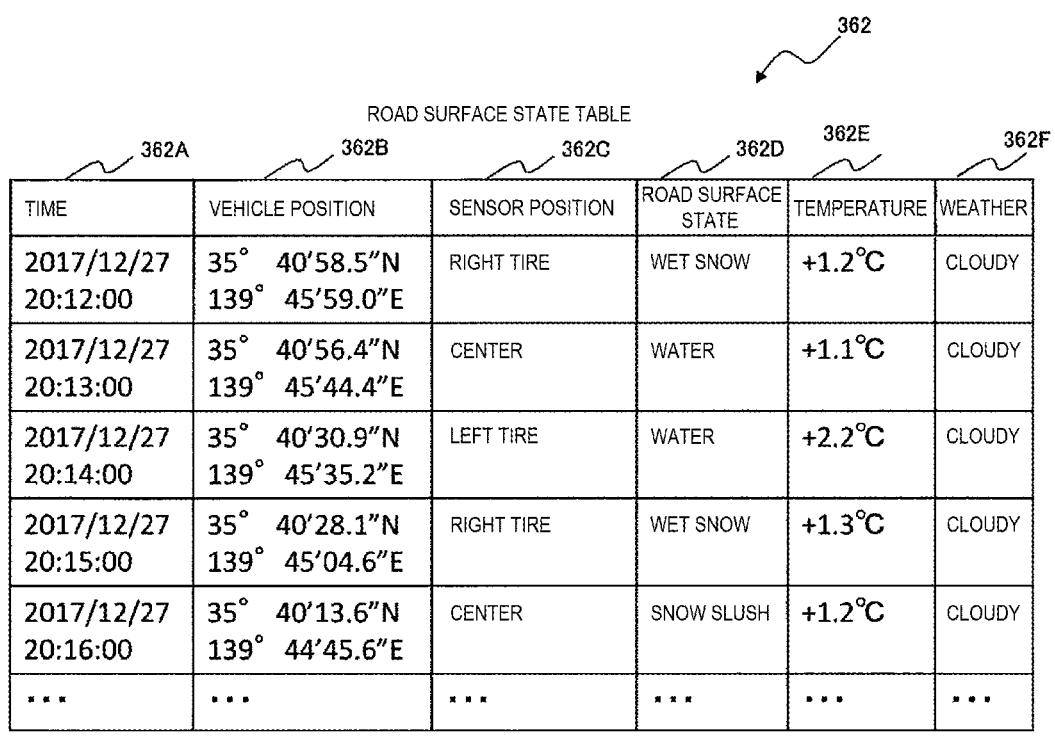
FIG. 9 is a diagram showing an example of a data structure of a road surface state table.

FIG. 9 is a diagram showing an example of a data structure of the road surface state table. The road surface state table 362 includes time 362A, a vehicle position 362B, a sensor position 362C, a road surface state 362D, temperature 362E, and weather 362F.

The time 362A is information for specifying a date and time when the vehicle 250 specifies position information and impedance information. The vehicle position 362B is coordinate information indicating a position of the vehicle 250 specified by the positioning system 118 of the road surface identification sensor 100. The sensor position 362C is information for specifying sensor positions (101A to 101E) on the bottom surface of the front bumper 250FB of the vehicle 250. The road surface state 362D is information for specifying a road surface medium. The temperature 362E and the weather 362F are information for specifying temperature and weather, and are information supplemented by the server device 350 inquiring a predetermined server device or the like that provides weather information at a later date.

A road surface medium specification unit 371 estimates a road surface medium for the impedance received from the communication unit 120 of the vehicle 250 by referring to the medium identification table 361 in which a medium estimated according to an impedance range has been associated with the impedance range beforehand. Then, the estimated road surface medium is stored in the road surface state table 362.

The server device 350 includes a similar hardware as the above-described hardware shown in FIG. 6. Specifically, the control unit 370 may be implemented by loading a predetermined program stored in the external storage device 53 into the memory 52 and executing the program by the CPU 51. The storage unit 360 may be implemented by using the memory 52 or the external storage device 53 by the CPU 51.

The predetermined program may be downloaded from the storage medium 54 to the external storage device 53 via the reading device 55, and then may be loaded into the memory 52 and executed by the CPU 51.

Alternatively, the predetermined program may be directly loaded from the storage medium 54 into the memory 52 via the reading device 55 and executed by the CPU 51.

The server device 350 is not limited thereto, and may be implemented by an application specific integrated circuit (ASIC), a microcomputer, or the like.

Figure 10:
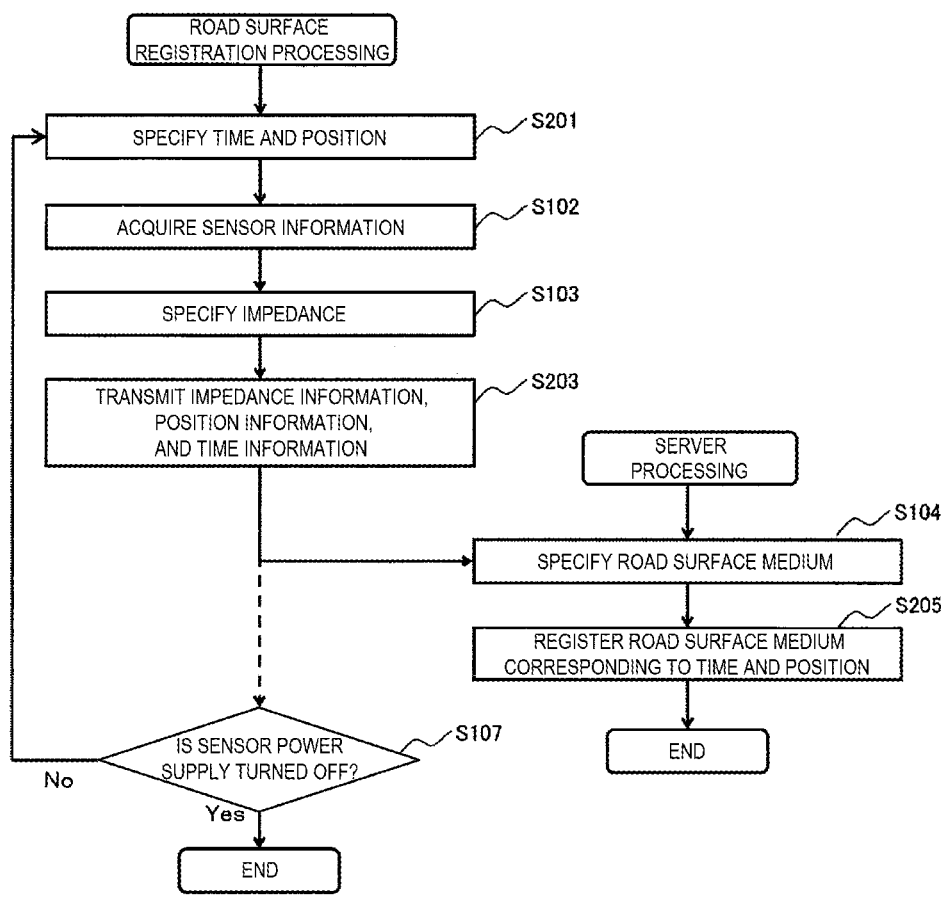
FIG. 10 is a flowchart showing an example of road surface registration processing.

FIG. 10 is a flowchart showing an example of road surface registration processing. The road surface registration processing is basically the same as the vehicle control processing. The road surface registration processing is started in the vehicle 250 at a predetermined frequency such as once every 10 seconds. The same step number is used for processing basically the same as the vehicle control processing in the following description.

First, the positioning system 118 of the road surface identification sensor 100 specifies time and a position (step S201). Specifically, the positioning system 118 receives information from a satellite such as a GPS and specifies a current location and time. Then, the impedance calculation device 117 acquires sensor information (step S102). Specifically, the impedance calculation device 117 acquires an amplitude ratio of reflected waves to traveling waves from the power detector 115 and a phase difference between the traveling waves and the reflected waves from the phase comparator 116.

Next, the impedance calculation device 117 specifies an impedance (step S103). Specifically, the impedance calculation device 117 calculates an impedance of the antenna 113 using the amplitude ratio and the phase difference acquired in step S102. Then, the communication unit 380 transmits the specified impedance information to the server device 350 (step S203). Specifically, the communication unit 380 transmits the impedance information, position information, and time information to the server device 350 via the network 950.

The road surface medium specification unit 371 of the server device 350 specifies a road surface medium (step S104). Specifically, the road surface medium specification unit 371 specifies a range to which the calculated impedance belongs by referring to the medium identification table 361, and specifies a predetermined medium in the range as a road surface medium in the vicinity of the antenna 113.

Then, the road surface medium specification unit 371 registers the road surface medium corresponding to the time and the position (step S205). Specifically, the road surface medium specification unit 371 registers the position information and the time information specified in step S201 and the road surface medium specified in step S104 into the road surface state table 362.

Next, the impedance calculation device 117 determines whether the system power supply is turned off (step S107). When the system power supply is turned off ("Yes" in step S107), the impedance calculation device 117 ends the road surface registration processing. When the system power supply is not turned off ("No" in step S107), the impedance calculation device 117 returns a control to step S201.

A flow of the road surface registration processing is described above. According to the road surface registration processing, information of the road surface medium can be acquired from the plurality of vehicles 250 and stored in the server device 350. Since the road surface identification sensor 100 used in the traveling control processing does not require other equipment such as a reflection plate in snow and can specify a medium in a non-contact manner, the road surface identification sensor 100 can be used for a general road surface and medium information can be collected more easily, widely and frequently.

Figure 11:
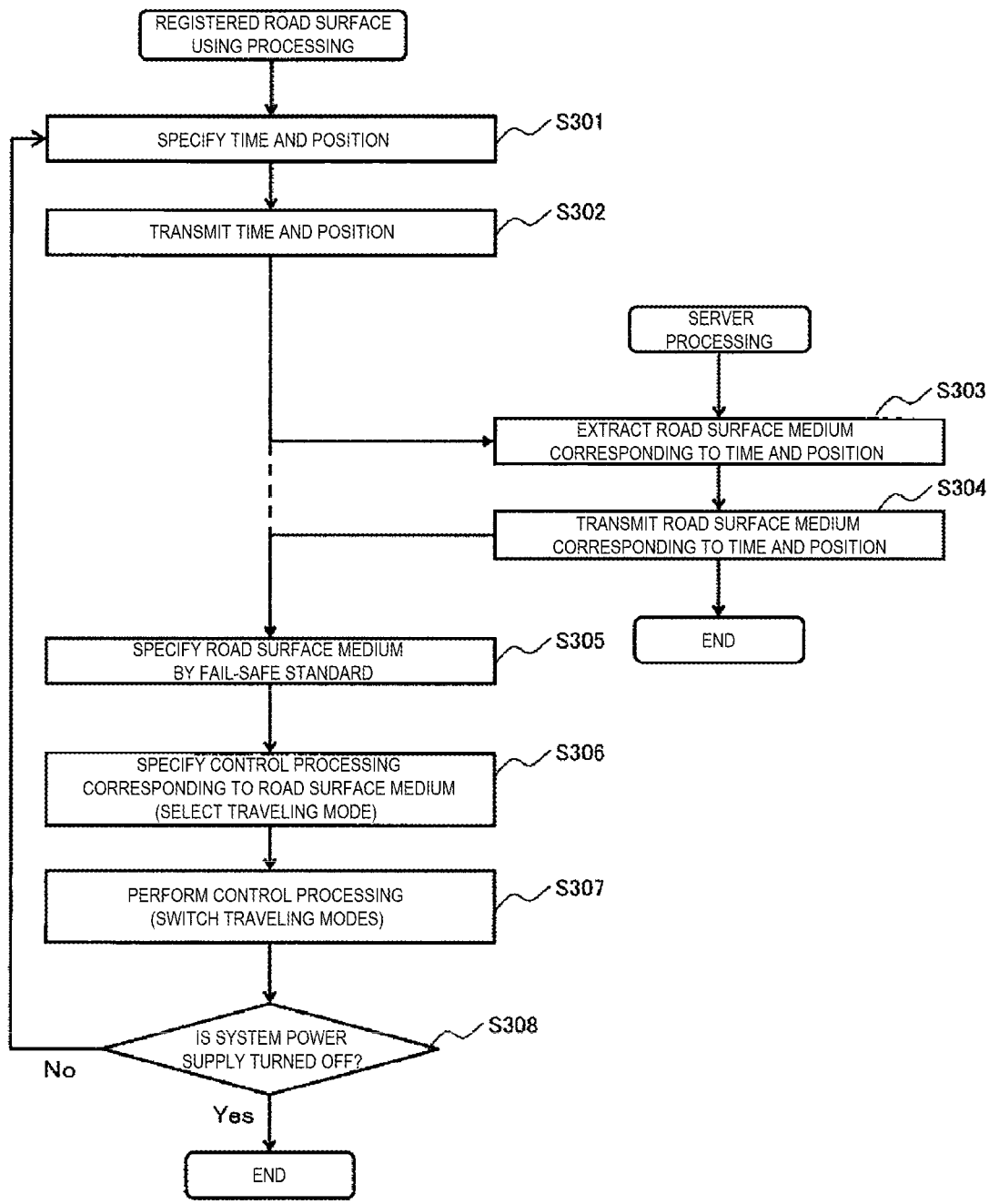
FIG. 11 is a flowchart showing an example of registered road surface using processing.

FIG. 11 is a flowchart showing an example of registered road surface using processing. The registered road surface using processing is started in the vehicle 250D at a predetermined frequency such as once every 60 seconds.

First, the positioning system 118 of the road surface identification sensor 100 specifies time and a position (step S301). Specifically, the positioning system 118 receives information from a satellite such as a GPS and specifies a current location and time.

Then, the communication unit 120 transmits the time and the position (step S302). Specifically, the communication unit 120 transmits the position information and the time information specified in step S301 to the server device 350 via the network 950.

Next, the road surface medium specification unit 371 of the server device 350 that has received the position information and the time information extracts a road surface medium corresponding to the time and the position (step S303). Specifically, the road surface medium specification unit 371 extracts a road surface medium in the vicinity (for example, a position within 200 m) of the received position and in the vicinity (for example, within 30 minutes) of the received time by referring to the road surface state table 362. In terms of extracting a road surface medium corresponding to time and a position, the invention is not limited thereto. For example, when a location where there is much freeze and accumulated snow and attention needs to be paid is known beforehand according to accident statistical data, near-miss information, or the like, a road surface medium in the vicinity of the location may be extracted as a target.

Then, the communication unit 380 transmits the road surface medium corresponding to the time and the position (step S304). Specifically, the communication unit 380 transmits the road surface medium in the vicinity extracted in step S303 to the traveling control unit 72D of the vehicle 250D via the network 950.

The traveling control unit 72D specifies the road surface medium by a fail-safe standard (step S305). Specifically, the traveling control unit 72D refers to the road surface medium in the vicinity transmitted in step S304, and specifies the road surface medium by the fail-safe standard. That is, a road surface medium satisfying least traveling conditions is specified among received road surface mediums. Without depending on the fail-safe standard, the traveling control unit 72D may specify a road surface medium by weighting or the like, or may simply specify a road surface medium by a majority decision.

Next, the traveling control unit 72D specifies control processing corresponding to the road surface medium (step S306). Specifically, the traveling control unit 72D specifies a traveling control in which an instruction is issued to an ECU, a brake, or the like (not shown) via a control network (not shown) according to the road surface medium.

Then, the traveling control unit 72D performs the control processing (step S307). Specifically, the traveling control unit 72D outputs an instruction of a predetermined traveling control corresponding to a traveling control mode specified in step S306 to the ECU or the like.

Next, the traveling control unit 72D determines whether the system power supply is turned off (step S308). When the system power supply is turned off ("Yes" in step S308), the traveling control unit 72D ends the registered road surface using processing. When the system power supply is not turned off ("No" in step S308), the traveling control unit 72D returns a control to step S301.

A flow of the registered road surface using processing is described above. According to the registered road surface using processing, since many pieces of information of the road surface medium in the vicinity of the antenna 113 that are acquired by vehicles in the vicinity of a host vehicle can be obtained via a network, the road surface medium can be specified more accurately. Alternatively, a road surface medium of the host vehicle can be estimated without using a road surface identification sensor of the host vehicle.

Figure 12:
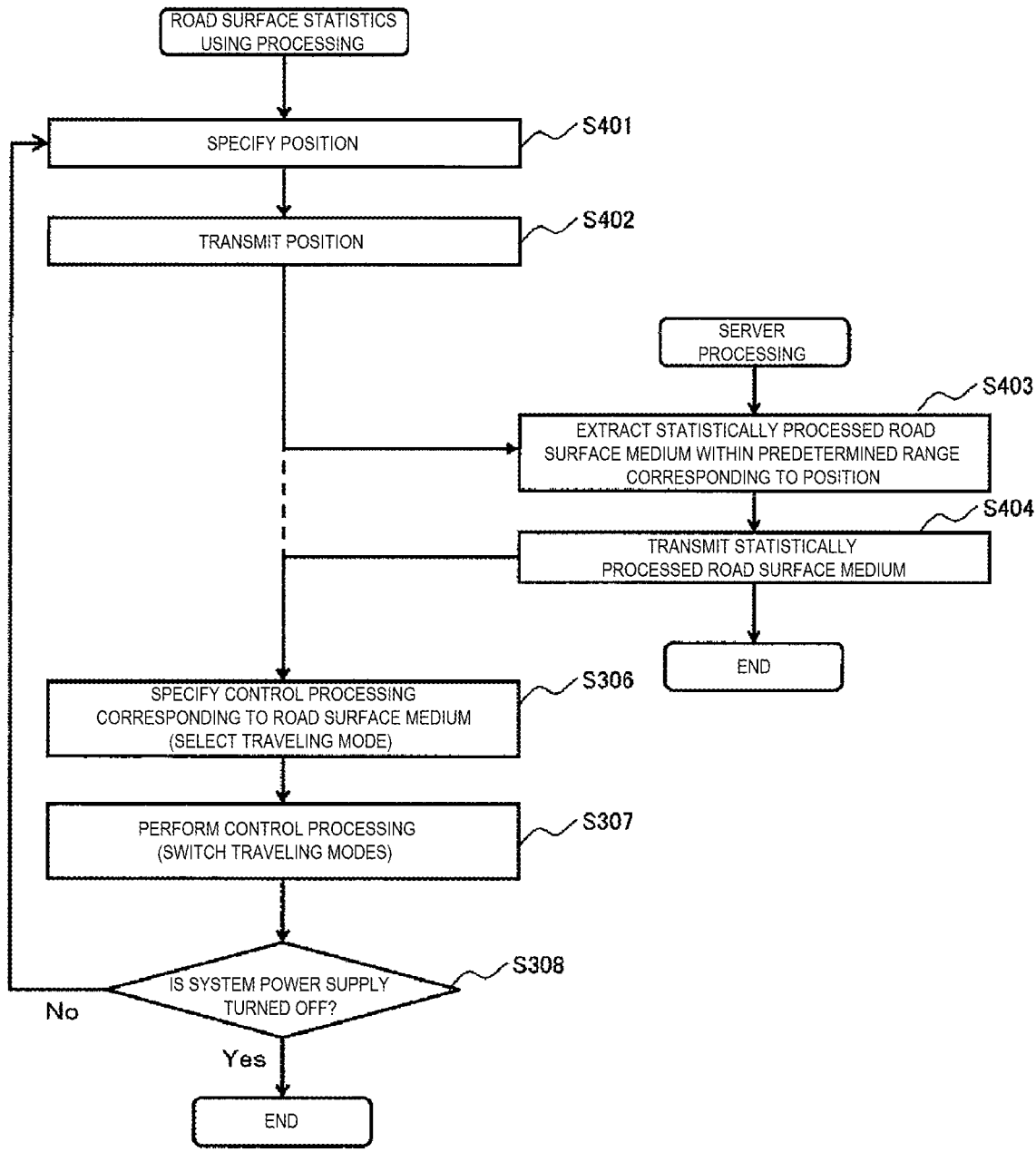
FIG. 12 is a flowchart showing an example of road surface statistics using processing.

FIG. 12 is a flowchart showing an example of road surface statistics using processing. The road surface statistics using processing is basically the same as the registered road surface using processing, and differs in terms of, for example, using road surface medium information subject to predetermined statistical processing (not shown) instead of using the road surface medium information as it is. The road surface medium information subject to statistical processing is stored in the road surface state table 362. The road surface statistics using processing is started in the vehicle 250D at a predetermined frequency such as once every 60 seconds.

First, the positioning system 118 of the road surface identification sensor 100 specifies a position (step S401). Specifically, the positioning system 118 receives information from a satellite such as a GPS and specifies a current location.

Then, the communication unit 120 transmits the position (step S402). Specifically, the communication unit 120 transmits the position information specified in step S401 to the server device 350 via the network 950.

Next, the road surface medium specification unit 371 of the server device 350 that has received the position information extracts a statistically processed road surface medium within a predetermined range (for example, a range within 1000 m or the like from the position, or a range in which traveling is estimated at a latest average speed within a predetermined period) corresponding to the position (step S403). Specifically, the road surface medium specification unit 371 refers to the road surface state table 362 to extract a medium at the time of processing for a road surface within a predetermined range (for example, if there is a preset route, a position along the route) based on the received position. In terms of extracting a road surface medium within a predetermined range corresponding to a position, the invention is not limited thereto. For example, when a location where there is much freeze and accumulated snow and attention needs to be paid is known beforehand according to accident statistical data, near-miss information, or the like, a road surface medium in the vicinity of the location may be extracted as a target.

Then, the communication unit 380 transmits the statistically processed road surface medium (step S404). Specifically, the communication unit 380 transmits the road surface medium extracted in step S403 to the traveling control unit 72D of the vehicle 250D via the network 950.

The traveling control unit 72D specifies control processing corresponding to the road surface medium (step S306), and performs the control processing (step S307). Specifically, the traveling control unit 72D outputs an instruction of a predetermined traveling control corresponding to the control processing specified in step S306 to an ECU or the like.

Next, the traveling control unit 72D determines whether the system power supply is turned off (step S308). When the system power supply is turned off ("Yes" in step S308), the traveling control unit 72D ends the road surface statistics using processing. When the system power supply is not turned off ("No" in step S308), the traveling control unit 72D returns a control to step S401.

A flow of the road surface statistics using processing is described above. According to the road surface statistics using processing, since statistically processed information of a road surface medium acquired in a similar past weather state and at a predetermined position can be obtained via a network, a medium on a remote road surface at an unreached position and on a future date and time can be specified. That is, a traveling control plan along a predetermined route can be made before departure, so that a smooth movement may be achieved.

An example of mounting a medium identification sensor to a vehicle is described above. A road surface medium at various positions instead of a predetermined position can be determined by mounting a medium identification sensor to a vehicle, and a traveling control can be performed more safely.

Figure 13:
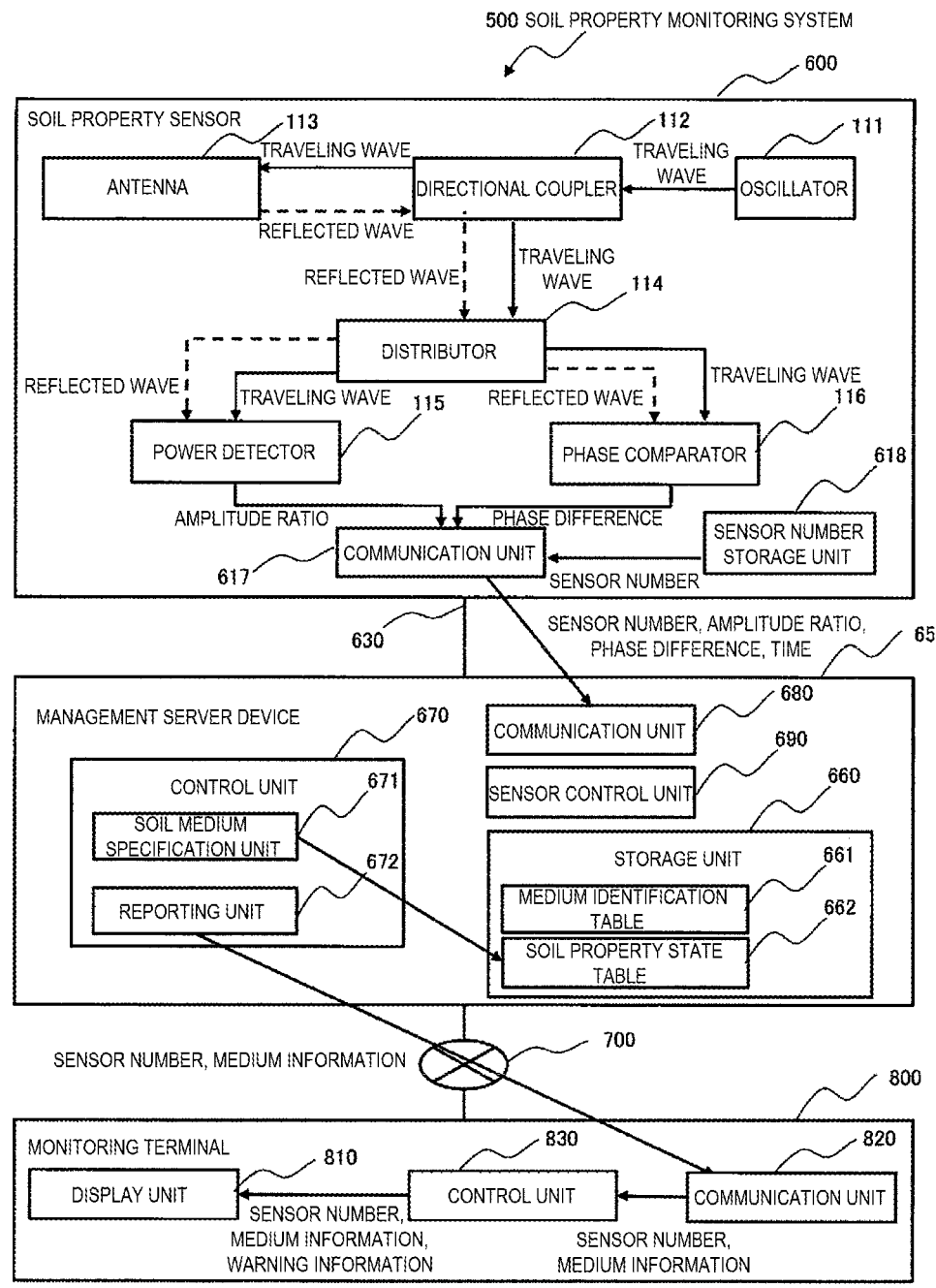
FIG. 13 is a diagram showing a configuration example of a soil property monitoring system.

FIG. 13 is a diagram showing a configuration example of a soil property monitoring system. A soil property monitoring system 500 includes a soil property sensor 600, a management server device 650 communicably connected with the soil property sensor 600 via a network 630, and a monitoring terminal 800 communicably connected with the management server device 650 via a monitoring network 700.

The soil property sensor 600 has substantially the same configuration as the road surface identification sensor 100 described above. Apart of the soil property sensor 600 is different from the road surface identification sensor 100. Hereinafter, the same configurations will be denoted by the same reference numerals, and descriptions thereof will be omitted.

The soil property sensor 600 includes the oscillator 111, the directional coupler 112, the antenna 113, the distributor 114, the power detector 115, the phase comparator 116, a communication unit 617, and a sensor number storage unit 618.

The communication unit 617 transmits information of a sensor number, and an amplitude ratio and a phase difference between the traveling waves and reflected waves of the antenna 113 to the management server device 650 via the network 630. The network 630 may be a public network such as a so-called Internet, or may be a closed network in which security is ensured.

A sensor number is a number for identifying an individual soil property sensor 600. The sensor number storage unit 618 stores a sensor number beforehand, and supplies the sensor number to the communication unit 617.

The management server device 650 includes a storage unit 660, a control unit 670, a communication unit 680, and a sensor control unit 690. The storage unit 660 includes a medium identification table 661 and a soil property state table 662.

Figure 14:
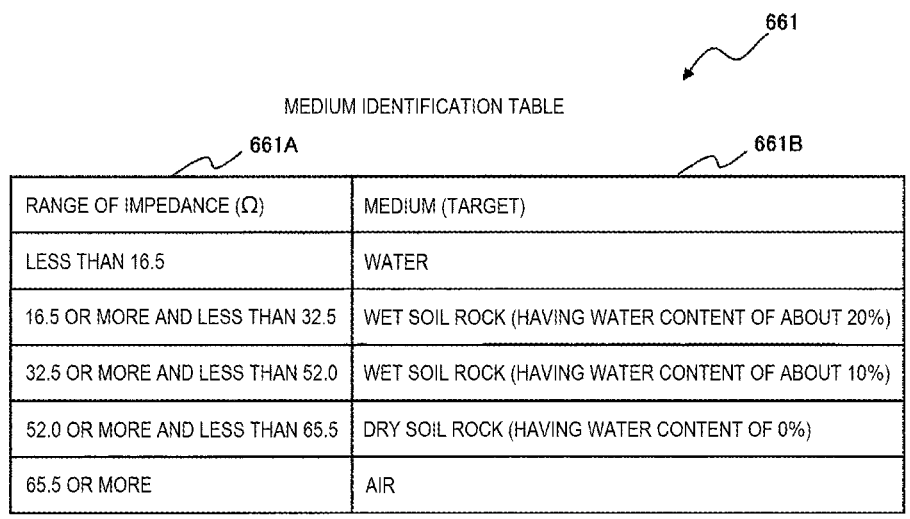
FIG. 14 is a diagram showing another example of a data structure of the medium identification table.

FIG. 14 is a diagram showing an example of a data structure of the medium identification table. In the medium identification table 661, an impedance range 661A that is information for specifying an impedance range and a medium 661B serving as a target medium are stored in association with each other. The medium identification table 661 stores information indicating, for example, "water" is present in the vicinity of the antenna 113 when an impedance is less than 16.5 ohms ($\Omega$), a so-called "wet soil rock (having a water content of about 20%)" is present in the vicinity of the antenna 113 when an impedance is 16.5$\Omega$ or more and less than 32.5$\Omega$. The information shown in FIG. 14 is just an example, and if there is a significant boundary value that can distinguish other mediums, an impedance range may be specified according to the value.

FIG. 15 is a diagram showing an example of a data structure of the soil property state table. The soil property state table 662 includes time 662A and soil property information for each sensor number 662B.

The time 662A is information for specifying a date and time when the soil property sensor 600 specifies a sensor number, and an amplitude ratio and a phase difference between traveling waves and reflected waves. The sensor number 662B is an identification result of a medium in the vicinity of each individual soil property sensor 600.

The control unit 670 includes a soil medium specification unit 671 and a reporting unit 672. The soil medium specification unit 671 calculates, for each soil property sensor 600, an impedance to be received via the communication unit 680, identifies a medium by referring to the medium identification table, and stores a medium identification result into the soil property state table 662. When the reporting unit 672 analyzes medium information stored in the soil property state table 662 and detects the soil property sensor 600 satisfying a predetermined condition, the reporting unit 672 notifies the monitoring terminal 800 of a sensor number of the soil property sensor 600 and the medium information via the monitoring network 700. The monitoring network 700 may be a public network such as a so-called Internet, or may be a closed network in which security is ensured.

The management server device 650 has a similar hardware as the above-described hardware shown in FIG. 6. Specifically, the control unit 670, the sensor control unit 690, and the communication unit 680 may be implemented by loading a predetermined program stored in the external storage device 53 into the memory 52 and executing the program by the CPU 51. The storage unit 660 may be implemented by using the memory 52 or the external storage device 53 by the CPU 51.

The predetermined program may be downloaded from the storage medium 54 to the external storage device 53 via the reading device 55, and then may be loaded into the memory 52 and executed by the CPU 51.

Alternatively, the predetermined program may be directly loaded from the storage medium 54 into the memory 52 via the reading device 55 and executed by the CPU 51.

The management server device 650 is not limited thereto, and may be implemented by an ASIC, a microcomputer, or the like.

The monitoring terminal 800 includes a display unit 810, a communication unit 820, and a control unit 830. The display unit 810 displays a sensor number, medium information, and warning information obtained from the control unit 830 on a display or the like. The communication unit 820 transmits and receives information including a report from the management server device 650 via the monitoring network 700. The control unit 830 receives an input and an output, acquires information obtained by the soil property sensor 600 via the communication unit 820, and calculates an average soil property during a predetermined period for each soil property sensor 600. The control unit 830 also determines a warning based on whether a difference between a current soil property and the average soil property during a predetermined period deviates from a standard difference.

The monitoring terminal 800 has a similar hardware as the above-described hardware shown in FIG. 6. Specifically, the display unit 810 and the communication unit 820 may be implemented by loading a predetermined program stored in the external storage device 53 into the memory 52 and executing the program by the CPU 51.

The predetermined program may be downloaded from the storage medium 54 to the external storage device 53 via the reading device 55, and then may be loaded into the memory 52 and executed by the CPU 51.

Alternatively, the predetermined program may be directly loaded from the storage medium 54 into the memory 52 via the reading device 55 and executed by the CPU 51.

The monitoring terminal 800 is not limited thereto, and may be implemented by an ASIC, a microcomputer, or the like.

Figure 16:
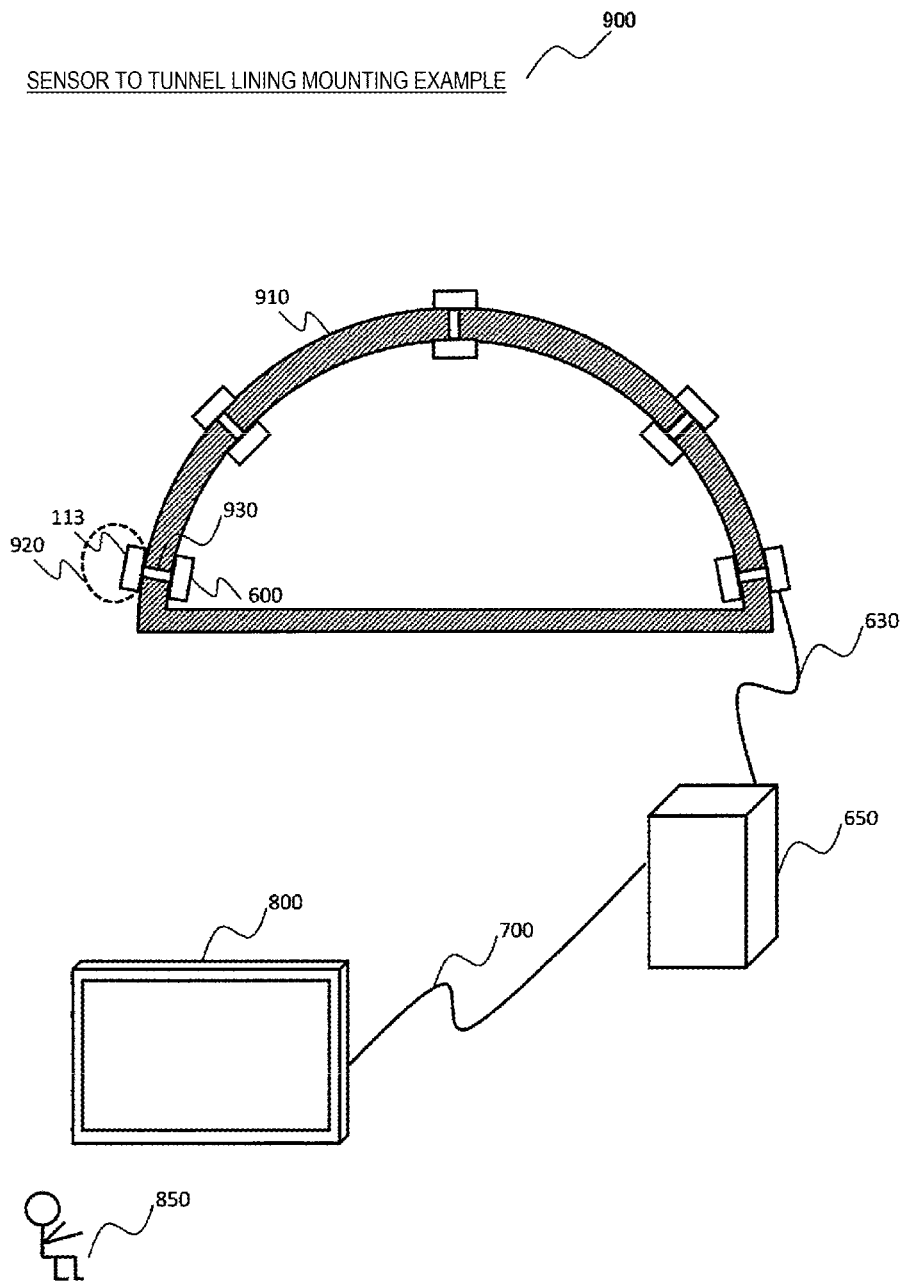
FIG. 16 is a diagram showing a sensor to tunnel lining mounting example.

FIG. 16 is a diagram showing a sensor to tunnel lining mounting example. In a sensor to tunnel lining mounting example 900, a tunnel lining 910 is provided with through holes passing through a back surface and an inner surface of the lining, the antenna 113 is provided on aback surface side of the tunnel, a coaxial cable 930 passes through a through hole to attach other members and the soil property sensor 600 on the inner surface of the lining. A soil property in the vicinity 920 of the antenna 113, that is, a soil medium on the back surface of the tunnel lining can be identified by attaching the soil property sensor 600 in such a manner. The soil property sensor 600 is preferably provided at a plurality of positions on the tunnel lining 910 as needed. The soil property sensor 600 is not limited to be attached to the tunnel lining 910, and may be provided underground. A supervisor 850 monitors a screen displayed on the monitoring terminal 800.

Figure 17:
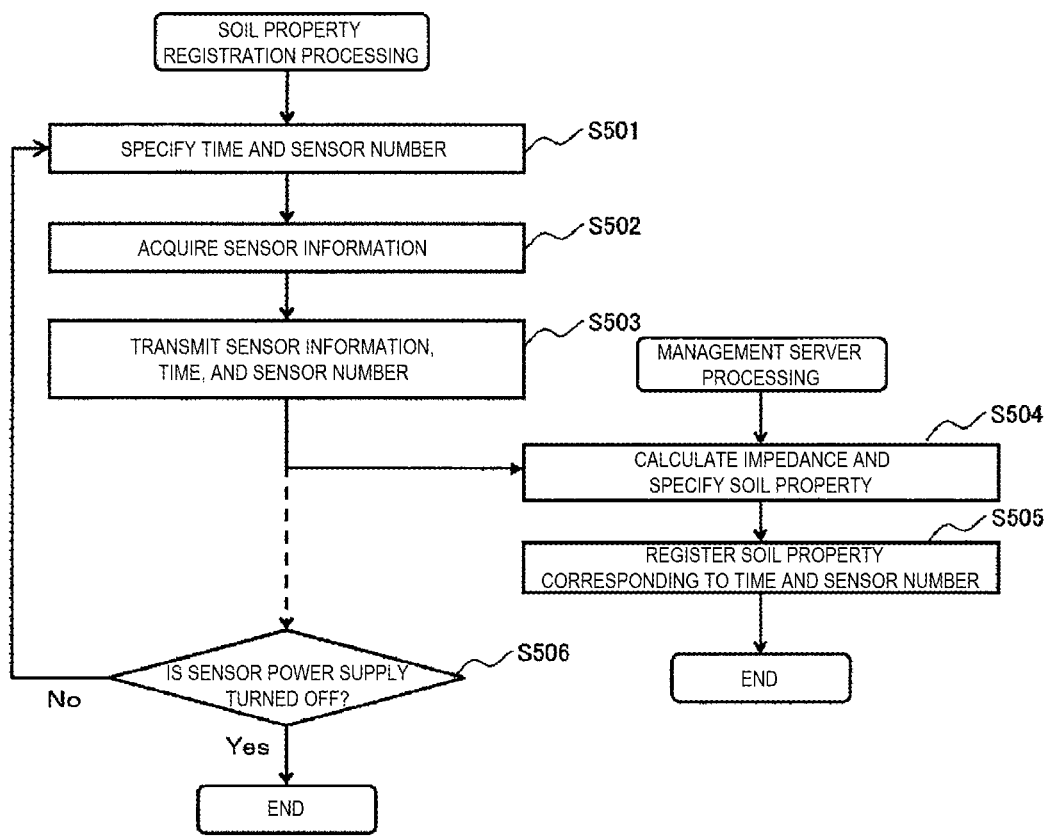
FIG. 17 is a flowchart showing an example of soil property registration processing.

FIG. 17 is a flowchart showing an example of soil property registration processing. The soil property registration processing is started in the soil property sensor 600 at a predetermined frequency such as once a day.

First, the communication unit 617 of the soil property sensor 600 specifies time and a sensor number (step S501). Specifically, the communication unit 617 acquires time from a timer (not shown) and acquires a sensor number from the sensor number storage unit 618. Then, the communication unit 617 acquires sensor information (step S502). Specifically, the communication unit 617 acquires an amplitude ratio of reflected waves to traveling waves from the power detector 15 and a phase difference between the traveling waves and the reflected waves from the phase comparator 16.

Then, the communication unit 617 transmits the sensor information (the amplitude ratio and the phase difference), the time, and the sensor number to the management server device 650 (step S503).

Next, the soil medium specification unit 671 of the management server device 650 calculates an impedance using the sensor information received via the communication unit 680, and specifies a soil property (step S504). Specifically, the soil medium specification unit 671 specifies a range to which the calculated impedance belongs by referring to the medium identification table 661, and specifies a predetermined medium in the range as a soil property in the vicinity of the antenna 113.

Then, the soil medium specification unit 671 registers the soil property corresponding to the time and the sensor number (step S505). Specifically, the soil medium specification unit 671 registers the time information and the sensor number specified in step S501 and the soil property specified in step S504 into the soil property state table 662.

Next, the communication unit 617 determines whether the system power supply is turned off (step S506). When the system power supply is turned off ("Yes" in step S506), the communication unit 617 ends the soil property registration processing. When the system power supply is not turned off ("No" in step S506), the communication unit 617 returns a control to step S501.

A flow of the soil property registration processing is described above. According to the soil property registration processing, soil property information can be acquired from a plurality of soil property sensors 600 and can be stored in the management server device 650. Since the soil property sensor 600 used in the soil property registration processing does not require other equipment such as a reflection plate in soil, and can specify a medium in a non-contact manner, and power consumption is low, the soil property sensor 600 can be used for a long period in a tunnel in which maintenance work is performed at limited timing, and soil property information can be collected more easily, widely and frequently.

Figure 18:
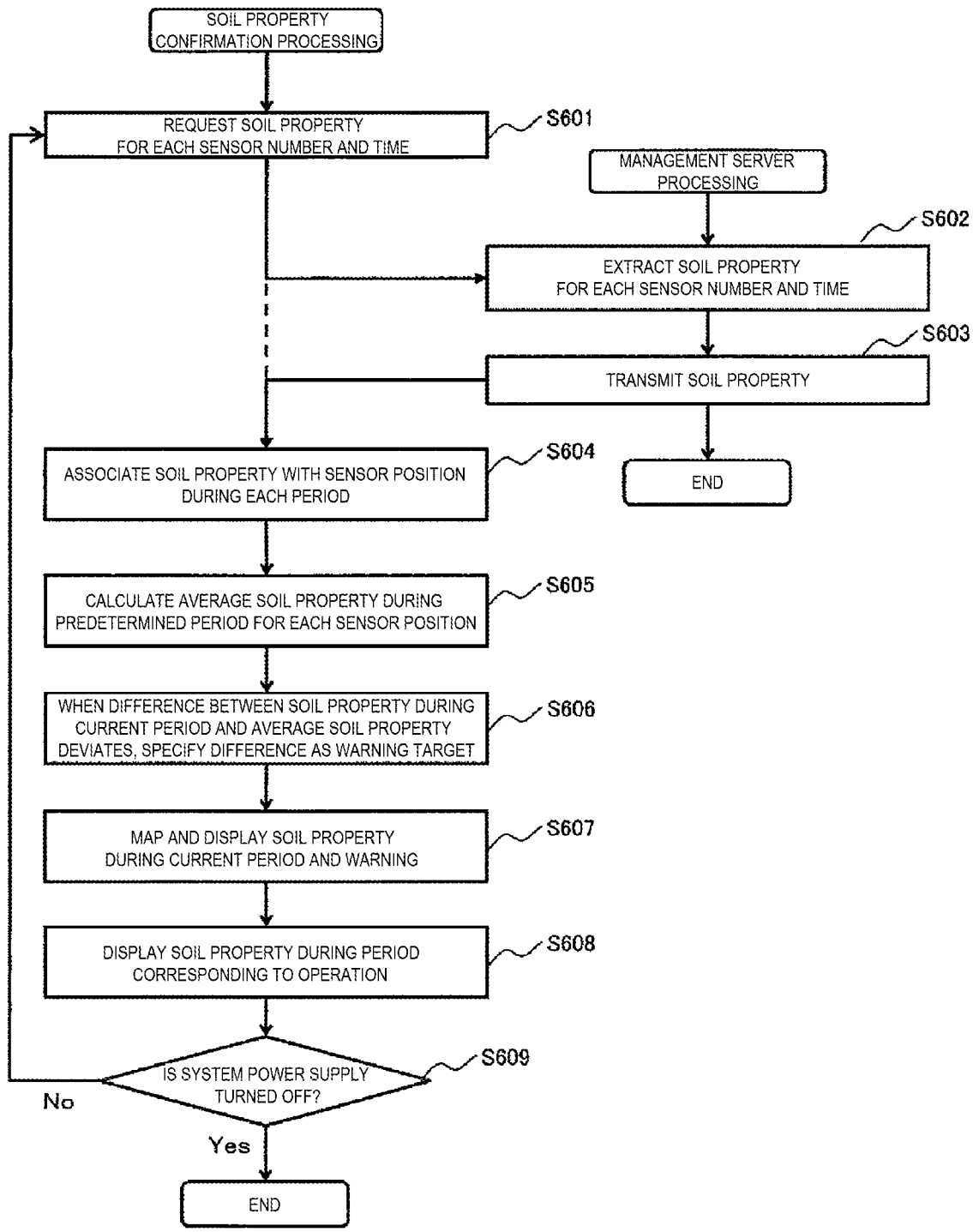
FIG. 18 is a flowchart showing an example of soil property confirmation processing.

FIG. 18 is a flowchart showing an example of soil property confirmation processing. The soil property confirmation processing is started when the monitoring terminal 800 is activated.

First, the control unit 830 of the monitoring terminal 800 requests a soil property for each sensor number and time (step S601). Specifically, the control unit 830 requests soil property information for each sensor number and time from the reporting unit 672 of the management server device 650 via the communication unit 820.

The reporting unit 672 extracts a soil property for each sensor number and time (step S602). Specifically, the reporting unit 672 acquires soil property information of a monitoring target including information of a sensor number and time by referring to the soil property state table 662.

Then, the reporting unit 672 transmits the extracted soil property information (step S603).

The control unit 830 associates a soil property with a sensor position during each period (step S604). Specifically, the control unit 830 distinguishes sensor information during each predetermined period (for example, a long past period such as last month, last three months, last six months, or a fixed period (a unit of three months)), and associates a sensor number with a sensor arrangement position in the tunnel.

Next, the control unit 830 calculates an average soil property during a predetermined period for each sensor position (step S605). Specifically, the control unit 830 averages a soil property at each arrangement position of the soil property sensor 600 during the predetermined period.

When a difference between a soil property during a current period and the average soil property deviates, the control unit 830 specifies the difference as a warning target (step S606). Specifically, the control unit 830 compares, for the same sensor position, a soil property at the current time with the average soil property during the predetermined period. When the soil property at the current time and the average soil property during the predetermined period have a significant difference from each other compared with a standard difference, the control unit 830 determines that the difference deviates and specifies the difference as a warning target. For example, when a soil property specified by a certain soil property sensor 600 is different from an average soil property during the last month by two or more stages, the difference is specified as a warning target since there is a sudden soil property change (a water content change).

Then, the display unit 810 maps and displays the soil property during a current period and a warning (step S607). Specifically, the display unit 810 acquires warning information, soil property information, and sensor position information from the control unit 830, displays the soil property information corresponding to a sensor position on a predetermined 3D display screen or the like, and performs an inversion display or a blinking display at a sensor position where there is a warning, or a predetermined display such as emphasis with a predetermined warning color.

Next, the display unit 810 displays a soil property during a period corresponding to an operation (step S608). Specifically, when the control unit 830 receives a slide input from a slidable time slide bar, or the like, the control unit 830 specifies a period corresponding to the slide operation, and displays an average soil property during this period on a display for each sensor position.

Next, the control unit 830 determines whether the system power supply is turned off (step S609). When the system power supply is turned off ("Yes" in step S609), the control unit 830 ends the soil property confirmation processing. When the system power supply is not turned off ("No" in step S609), the control unit 830 returns a control to step S601.

A flow of the soil property confirmation processing is described above. According to the soil property confirmation processing, the monitoring terminal 800 can acquire soil property information acquired from a plurality of soil property sensors 600 from the management server device 650 and check the soil property information on the monitoring terminal. When a sudden change is recognized as compared with information obtained by statistically processing changes of past soil properties, a warning can be displayed. Past soil property information during a predetermined period can be more easily averaged and referred to.

Figure 19:
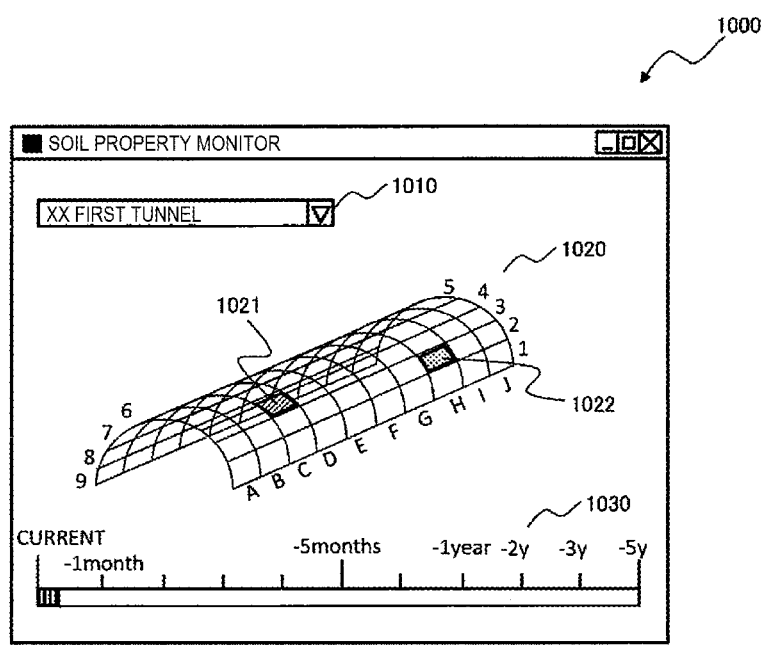
FIG. 19 is a diagram showing an example of an output screen of the soil property confirmation processing.

FIG. 19 is a diagram showing an example of an output screen of the soil property confirmation processing. Specifically, an output screen 1000 shows an example of an output screen of the soil property confirmation processing in step S607. The output screen 1000 includes a monitoring target selection input reception area 1010, a monitoring target display 3D model 1020, warning sensor positions 1021 and 1022, and a time slide bar 1030.

The monitoring target selection input reception area 1010 receives a selection input of a structure (a tunnel) to be monitored in a pull-down manner. The monitoring target display 3D model 1020 displays a 3D model of the structure (the tunnel) to be monitored. The 3D model is a frame display of a three-dimensional object using an existing computer aided design (CAD) viewer or the like, and can be rotated and displayed in three axial directions (horizontal X and Y directions, a vertical Z direction, and the like). The warning sensor positions 1021 and 1022 respectively display sensor information with a warning in a highlighted manner according to a sensor position on the 3D model.

The time slide bar 1030 is a slide bar in which time is plotted on a straight line to show a current sensor state at a left end and an oldest sensor state at a right end. By dragging the slide bar to the left or the right, an average soil property displayed for each sensor position on the monitoring target display 3D model 1020 can be set to a period corresponding to the slide operation.

An embodiment according to the invention is described above. According to the embodiment of the invention, a medium can be specified more simply.

The embodiments described above have been described in detail for easy understanding of the invention, and the invention is not necessarily limited to those including all the configurations described above. A part of configurations of one embodiment can be replaced with another configuration, and the configuration of one embodiment can also be added to the configuration of another embodiment. A part of the configurations of the embodiment may be deleted.

The units, the configurations, functions, processing units, and the like described above may be partially or entirely implemented by hardware such as through a design using an integrated circuit. The units, configurations, functions, and the like described above may be implemented by software by a processor interpreting and executing a program that implements respective functions. Information such as a program, a table, and a file for implementing each function can be placed in a recording device such as a memory and a hard disk, or a recording medium such as an IC card, an SD card, and a DVD.

Control lines and information lines according to the embodiment described above indicate what is considered necessary for description, and not all the control lines and the information lines are necessarily shown in a product. In practice, it may be considered that almost all the configurations are connected to each other. As described above, the invention has been described centering on the embodiment.

REFERENCE SIGN LIST 10 medium identification sensor
11 oscillator
12 directional coupler
13 antenna
14 distributor
15 power detector
16 phase comparator
17 medium specification processing device
60 storage unit
61 medium identification table
80 output device

The invention claimed is:

1. A medium sensor device comprising:
an antenna;
a storage unit that stores a medium identification table in which a medium corresponding to an impedance of the antenna has been determined beforehand; and
a medium specification unit that specifies an impedance of the antenna and specifies a medium in the vicinity of the antenna by referring to the medium identification table.

2. The medium sensor device according to claim 1, wherein
the medium specification unit specifies a power amplitude ratio and a phase difference by acquiring traveling waves and reflected waves of the antenna from a directional coupler, and specifies the impedance.

3. A road surface identification sensor device mounted in a vehicle, the road surface identification sensor device comprising:
an antenna;
an impedance calculation unit that calculates an impedance by using an amplitude ratio and a phase difference between traveling waves and reflected waves of the antenna; and
a positioning system that specifies position information.

4. A road surface monitoring system mounted in a vehicle, the road surface monitoring system comprising:
a control device; and
one or a plurality of road surface identification sensors, wherein
each of the road surface identification sensors includes:
an antenna,
an impedance calculation device that calculates an impedance of the antenna, and
a positioning system that specifies position information, and
the control device includes:
a storage unit that stores a medium identification table in which a medium corresponding to the impedance has been determined beforehand,
a road surface medium specification unit that specifies a road surface medium in the vicinity of the antenna by referring to the medium identification table and using the impedance, and
a traveling control unit that performs a predetermined traveling control on the vehicle according to the road surface medium.

5. The road surface monitoring system according to claim 4, wherein
the road surface identification sensor is at least mounted in the vicinity of a ground contact surface of each front tire of the vehicle.

6. A road surface monitoring system comprising:
one or a plurality of road surface identification sensors mounted in one vehicle or each of a plurality of vehicles; and
a server device that acquires information from the road surface identification sensors via communication, wherein
a part or all of the vehicles include a traveling control unit that performs a traveling control using road surface medium information acquired from the server device via communication,
each of the road surface identification sensors includes:
an antenna,
an impedance calculation device that calculates an impedance of the antenna, and
a positioning system that specifies position information, and
the server device includes:
a storage unit that stores a medium identification table in which a medium corresponding to the impedance has been determined beforehand and a road surface state table in which the medium is stored as a road surface state according to a position and time, and
a road surface medium specification unit that specifies a road surface medium in the vicinity of the antenna by referring to the medium identification table and using the impedance and stores the road surface medium in the road surface state table in association with the position information.

7. The road surface monitoring system according to claim 6, wherein
the traveling control unit acquires one or a plurality of pieces of information of road surface medium in the vicinity of the antenna, the information being in a latest time range at the same past date and acquired from the server device via communication, and performs a traveling control corresponding to a medium on a road surface that is unsuitable for traveling.

8. A soil property sensor device comprising:
an antenna embedded in soil; and
a communication unit that transmits an amplitude ratio and a phase difference between traveling waves and reflected waves of the antenna to a predetermined external server device.

9. A soil property monitoring system comprising:
a storage unit that stores a medium identification table in which a medium corresponding to an impedance has been determined beforehand; and
a soil medium specification unit that, when an amplitude ratio and a phase difference between traveling waves and reflected waves of the antenna are received from the soil property sensor device according to claim 8, calculates an impedance and specifies a soil property in the vicinity of the antenna by referring to the medium identification table.

10. A soil property monitoring system comprising:
one or a plurality of soil property sensors;
a management server device; and
a monitoring terminal, wherein each of the soil property sensors includes:
- an antenna embedded in soil, and
- a communication unit that transmits an amplitude ratio and a phase difference between traveling waves and reflected waves of the antenna to the management server device, the management server device includes:
- a storage unit that stores a medium identification table in which a medium corresponding to an impedance has been determined beforehand, and
- a soil medium specification unit that, when an amplitude ratio and a phase difference between traveling waves and reflected waves of the antenna are received from the soil property sensors, calculates an impedance and specifies a soil property in the vicinity of the antenna by referring to the medium identification table, and the monitoring terminal includes:
- a display unit that displays the soil property specified by the management server device according to an arrangement of the soil property sensors.

11. The soil property monitoring system according to claim 10, wherein
- the storage unit stores a soil property state table in which the soil property is stored according to the soil property sensors and time,
- the soil medium specification unit stores the soil property in the soil property state table in association with the soil property sensors and time, and
- the display unit of the monitoring terminal displays a time-series change of the soil property specified by the management server device according to the arrangement of the soil property sensors.

12. The soil property monitoring system according to claim 10, wherein
- the antenna is provided on a back surface of a tunnel lining, and
- the communication unit is provided on an inner surface of the tunnel lining.

\* \* \* \* \*